United States Patent [19]

Lee et al.

[11] Patent Number: 4,845,037

[45] Date of Patent: Jul. 4, 1989

[54] PROCESS FOR PRODUCING ANTIBIOTIC LL-D42067α

[75] Inventors: Taikwang M. Lee, Cranbury, N.J.; Joseph J. Goodman, Rockland, N.Y.; Michael Greenstein, Rockland, N.Y.; Donald B. Borders, Rockland, N.Y.

[73] Assignee: American Cyanamid Company, Stamford, Conn.

[21] Appl. No.: 891,082

[22] Filed: Jul. 31, 1986

[51] Int. Cl.$^4$ .................... C12N 1/00; C12P 17/16; C12P 17/18

[52] U.S. Cl. ................... 435/252.1; 435/118; 435/867; 435/119

[58] Field of Search ............... 435/119, 118, 253, 170, 435/867.

[56] References Cited

U.S. PATENT DOCUMENTS 4,551,533  11/1985  Lee et al. ............................ 435/825
4,639,467  1/1987  Celino .................................. 514/468

Primary Examiner—Charles F. Warren
Assistant Examiner—Irene Marx
Attorney, Agent, or Firm—Alice C. Brennan

[57] ABSTRACT

A biologically pure culture of *Micromonospora purpureochromogenes* ssp. Wuxiensis and its use in an aerobic fermentation process to produce the antibacterial and antiparasitic agent LL-D42067α.

5 Claims, No Drawings

PROCESS FOR PRODUCING ANTIBIOTIC LL-D42067α

SUMMARY OF THE INVENTION

This invention consists of a process for producing the antibiotic LL-D42067α by aerobic fermentation, using a strain of a new subspecies of *Micromonospora purpureochromogenes* ssp. Wuxiensis, NRRL 18075.

BACKGROUND OF THE INVENTION

The antibacterial and antiparasitic agent LL-D42067α is described and claimed in U.S. Pat. No. 4,551,533, which is incorporated by reference herein. This patent describes the antibiotic LL-D42067α in terms of structure, physico-chemical characteristics and utility and presents claims to the compound and a process for its production by aerobic fermentation using the culture *Actinomadura madurae* subspecies simaoensis NRRL 15734.

DETAILED DESCRIPTION OF THE INVENTION

This invention is concerned with a process for producing the antibiotic LL-D42067α during the cultivation under controlled conditions of a new strain of a new subspecies of *Micromonospora purpureochromogenes*. This new strain is maintained in the culture collection of the Medical Research Division, American Cyanamid Company, Pearl River, N.Y. as culture number LL-F29092. A viable culture of this new microorganism has been deposited with the Patent Culture Collection Laboratory, Northern Regional Research Center, U.S. Department of Agriculture, Peoria, Ill. 61604, and has been added to its permanent collection for maintenance pursuant to requirements imposed by the United States Patent and Trademark Office. It is freely available to the public in this depository under its accession number NRRL 18075.

Culture LL-F29092 was isolated from a soil sample from Wuxi in the People's Republic of China. The culture was taxonomically characterized and was identified as a new subspecies of *Micromonospora purpureochromogenes*, designated *Micromonospora purpureochromagenes* ssp. Wuxiensis.

An examination of the morphology of microorganism LL-F29092 indicated that it belonged to the genus Micromonospora as confirmed by whole cell analysis which demonstrated the presence of xylose and arabinose (=whole cell sugar type 1) and the meso isomer of diaminopimelic acid.

Physiologically, using the International Streptomyces Project carbohydrate utilization tests, Table I, LL-F29092 resembled *Micromonospora purpureochromogenes* as represented by the type strain ATCC 27007.

TABLE I

Comparison of LL-F29092 with *M. purpureochromogenes* ATCC 27007 in the ISP Carbohydrate Utilization Tests

| Carbohydrate | LL-F29092 | *M. purpureochromogenes* ATCC 27007 |
| --- | --- | --- |
| Arabinose | − | − |
| Cellulose | − | − |
| Fructose | + | + |
| Glucose | + | + |
| Inositol | − | − |
| Mannitol | − | − |
| Raffinose | + | + |
| Rhamnose | − | − |
| Sucrose | + | + |
| Xylose | + | + |

In the Gordon test series, Table II, LL-F29092 differed in four characters from *M. purpureochromogenes* ATCC 27007, notably amylase and nitrate reductase production and production of acid from α-methyl-D-glucoside and erythritol.

TABLE II

Comparison of LL-F29092 and *M. purpureochromogenes* ATCC 27007 in Gordon Test Reactions

| Comparison | LL-F29092 | *M. purpureochromogenes* ATCC 27007 |
| --- | --- | --- |
| Degradation/Transformation of | | |
| Casein | ±(slow) | + |
| Xanthine | − | − |
| Hypoxanthine | − | − |
| Tyrosine | + | + |
| Adenine | − | Variable |
| Production of | | |
| Amylase | + | − |
| Gelatinase | + | + |
| Phosphatase | + | + |
| Nitrate Reductase | + | − |
| Urease | − | − |
| Esculinase | + | + |
| Growth on/in | | |
| 5% Sodium chloride | Variable | − |
| Salicylate | − | Variable |
| Lysozyme Broth | − | − |
| Utilization | | |
| Acetate | + | + |
| Benzoate | − | − |
| Citrate | ± | ± |
| Lactate | + | + |
| Malate | + | + |
| Mucate | − | − |
| Oxalate | − | − |
| Propionate | + | + |
| Pyruvate | + | + |
| Succinate | + | + |
| Tartrate | − | − |
| Growth at | | |
| 10° C. | + | + |
| 42° C. | + | + |
| 45° C. | − | − |
| Acid from | | |
| Adonitol | − | − |
| Arabinose | − | − |
| Cellobiose | + | + |
| Dextrin | + | + |
| Dulcitol | − | − |
| Erythritol | − | + |
| Fructose | + | + |
| Galactose | + | + |
| Glucose | + | + |
| Glycerol | + | + |
| Inositol | − | − |
| Lactose | + | + |
| Maltose | + | + |
| Mannitol | − | − |
| Mannose | + | + |
| Melibiose | + | + |
| α-Methyl-D-Glucoside | − | + |
| Raffinose | + | + |
| Rhamnose | − | − |
| Salicin | + | + |
| Sorbitol | − | − |
| Sucrose | + | + |

TABLE II-continued

Comparison of LL-F29092 and *M. purpureochromogenes* ATCC 27007 in Gordon Test Reactions

| Comparison | LL-F29092 | *M. purpureochromogenes* ATCC 27007 |
|---|---|---|
| Trehalose | + | + |
| Xylose | + | + |
| β-Methyl-D-Xyloside | − | − |

Macromorphologically LL-F29092 and *M. purpureochromogenes* ATCC 27007 were somewhat different, Table III. By electron microscopy the spores of both strains were found to be warty.

TABLE III

Comparison of the Macromorphology of LL-F29092 and *M. purpureochromogenes* ATCC 27007  2 Weeks at 28° C.

| Agar Medium | LL-F29092 | *M. purpureochromogenes* ATCC 27007 |
|---|---|---|
| Bennett's | Black spore layer<br>Slight black-brown soluble pigment | Black spore layer<br>Brown-black soluble pigment |
| Bennett's-Dextrin | Black spore layer<br>No soluble pigment | Black spore layer<br>Brown-black soluble pigment |
| Czapek's | No spore layer<br>Colorless to light orange vegetative<br>No soluble pigment | No spore layer<br>Light brownish-tan vegetative<br>Light brown-tan soluble pigment |
| Nutrient | Slight black spore layer<br>Light orange vegetative<br>No soluble pigment | Slight black spore layer<br>Light orange vegetative<br>No soluble pigment |
| Oatmeal | Green-black spore layer<br>Soluble greenish-black pigment | No spore layer<br>Beige vegetative hyphae<br>Fair soluble black pigment |
| Potato-Dextrose | Black spore layer<br>No soluble pigment | No spore layer<br>Light orange vegetative hyphae<br>No soluble pigment |
| ATCC 635 | Black spore layer<br>No soluble pigment | Black spore layer<br>Brownish-black soluble pigment |
| Yeast-Czapeks | Slight black spore layer<br>Orange vegetative hyphae<br>Yellow-brown soluble pigment | Black spore layer<br>Brown-black soluble pigment |
| Yeast-Dextrose | Sparse black spore layer<br>Orange vegetative hyphae<br>No soluble pigment | Black spore layer<br>Brown-black soluble pigment |
| Yeast-Malt | Black spore layer<br>Black soluble pigment | Black spore layer<br>Brown-black soluble pigment |

For the production of the antibacterial and antiparasitic agent LL-D42067α, the present invention is not limited to this particular organism or to organisms fully answering the above growth and microscopic characteristics, which are given for illustrative purposes only. In fact, it is desired and intented to include the use of naturally-occurring mutants of this organism as well as induced mutants produced from this organism by various mutagenic means known to those skilled in the art, such as exposure to nitrogen mustard, x-ray radiation, ultraviolet radiation, N'-methyl-N'-nitro-N-nitrosguanidine, actinophages and the like. It is also desired and intended to include inter- and intraspecific genetic recombinants produced by genetic techniques known to those skilled in the art such as, for example, conjugation, transduction and genetic engineering techniques.

The antibiotic LL-D42067α was derived by the general fermentation and isolation techniques described in U.S. Pat. No. 4,551,533 using spores of *Micromonospora purpureochromogenes* ssp. Wuxiensis NRRL 18075.

The following specific examples illustrate this procedure but are not to be construed as limiting the invention.

EXAMPLE 1

Inoculum Preparation

A typical medium used to grow the primary inoculum was prepared according to the following formula:

| | |
|---|---|
| Yeast extract | 0.5% |
| N-Z Amine A ® * | 0.5% |
| Dextrin | 2.0% |
| Dextrose | 1.0% |
| Calcium carbonate | 0.1% |
| Water qs | 100% |

This medium was adjusted to pH 6.8 and then sterilized. A 100 ml portion of this sterile medium, in a 500 ml flask, was inoculated with mycelial scrapings from an agar slant of *Micromonospora purpureochromogenes* ssp. Wuxiensis, NRRL 18075. The medium was then placed on a rotary shaker and agitated vigorously at 28° C. for 48 hours. This primary inoculum was then used to inoculate 1 liter of the same sterile medium in a 2 liter bottle. This medium was grown at 32° C. for 48 hours providing secondary inoculum.

EXAMPLE 2

Tank Fermentation

A fermentation medium of the following formulation was prepared:

| | |
|---|---|
| Yeast extract | 1.0% |
| N-Z Amine A ® * | 0.5% |
| Dextrin | 2.0% |
| Dextrose | 1.0% |
| Calcium carbonate | 0.4% |
| Water qs | 100% |

*A pancreatic digest of casein, registered trademark of Sheffield Chemical, Norwich, NY.

A 26 liter portion of this medium in a 30 liter tank was adjusted to pH 6.8 with aqueous sodium hydroxide, then sterilized and inoculated with 1 liter of the secondary inoculum from Example 1. The fermentation was maintained at 30° C. with a sterile air flow of 30 liters per liter of medium per minute and agitation by an impeller operated at 550 rpm for 66 hours at which time the fermentation was harvested.

EXAMPLE 3

Isolation of LL-D42067α

Thirteen liters of the whole harvest broth from Example 2 were combined with an equal volume of ethyl acetate, mixed for 1 hour and filtered through diatomaceous earth. The two phase filtrate was separated. The ethyl acetate layer was concentrated to dryness in vacuo giving 26.5 g of solid.

This solid was mixed with 100 ml of dichloromethane and 2500 ml of methanol to obtain two phases. The lower phase containing lipids was discarded and the upper phase was concentrated to dryness to give 2.4 g of crude residue. The residue was chromatographed on a dry packed 8 inch×¾ inch column of silica gel and eluted with ethyl acetate:chloroform (7:3) and 5 ml fractions were collected. Fractions 23–65, which were active against *Bacillus subtilis* (Stansly R-78) by an agar diffusion assay, were pooled and concentrated to give 0.9 g of crude LL-D42067α. This 0.9 g was redissolved in acetone. The solution was filtered and the filtrate evaporated, giving 0.5 g of solid. This solid was chromatographed on a dry packed column (0.5 inch×10 inch) of Woelm silica gel eluted with dichloromethane:1% acetic acid in methanol (9:1) as 1 ml fractions were collected. LL-D42067α eluted in the first six fractions. The active fractions were combined and further purified by semi-preparative HPLC using a reverse phase column (C18, 7.8 mm×30 cm; Waters Associates) with a mobile phase of acetonitrile:0.1M ammonium acetate (35:65), pH 4.5 at a flow rate of 4 ml/minute. The detection was made by UV at 365 and 405 nm and the retention time of LL-D42067α was recorded as 13 minutes. The yield was 3 mg of pure LL-D42067α which was identified by infrared, ultraviolet, proton nuclear magnetic resonance and mass spectrum and found to be identical with standard LL-D42067α.

EXAMPLE 4

Flask Fermentation

A frozen vegetative suspension of *Micromonospora purpureochromogenes* ssp. Wuxiensis NRRL 18075 was used to inoculate 100 ml of the same sterile medium as in Example 1, in a 500 ml flask and grown for 3 days at 28° C. on a rotary shaker. This primary inoculum was used to inoculate a second stage of the same medium which was incubated for 4 days at 28° C. on a rotary shaker.

This secondary inoculum was used to inoculate twenty flasks, each containing 100 ml of the below described sterile fermentation medium at the rate of 5% v/v.

| | |
|---|---|
| Calcium carbonate | 0.3% |
| Sucrose | 8.0% |
| Corn steep liquor | 1.0% |
| Soyflour | 1.0% |
| Cottonseed flour | 1.0% |
| Water qs | 100.0% |

These fermentation flasks were incubated at 32° C. for 7 days on a rotary shaker, then harvested and the harvest mashes pooled giving a total of 2 liters.

A 1 liter portion of this fermentation was filtered through diatomaceous earth. This filtrate and the other 1 liter of harvest broth were then each treated separately but identically as follows: Each was extracted with 5% of 2N hydrochloric acid in butanol. Each extract was purified by HPLC. An ultraviolet scan of the appropriate HPLC fraction showed 1.3 μg/ml of authentic LL-D42067α in the acid butanol extraction of the filtrate.

What is claimed is:

1. A process for producing antibiotic LL-D42067α which comprises aerobically fermenting the microorganism *Micromonospora purpureochromogenes* ssp. Wuxiensis, having the deposit accession number NRRL 18075 or an antibiotic LL-D42067α-producing mutant thereof, in a liquid medium containing assimilable sources of carbon, nitrogen and inorganic anion and cation salts, until a substantial amount of LL-D42067α is produced in said medium and then recovering the antibiotic therefrom.

2. A process for producing antibiotic LL-D42067α which comprises aerobically fermenting a liquid medium containing assimilable sources of carbon, nitrogen and inorganic anion and cation salts, which medium has been inoculated with a viable culture of the microorganism *Micromonospora purpureochromogenes* ssp. Wuxiensis, having the deposit accession number NRRL 18075, or an antibiotic LL-D42067α-producing mutant thereof, maintaining said fermentation culture with sterile aeration and agitation at a temperature of 24°–32° C. and a pH of 7.0–7.6 for a period of 60–200 hours, harvesting the broth and extracting the antibiotic.

3. A biologically pure culture of the microorganism *Micromonospora purpureochromogenes* ssp. Wuxiensis having the deposit accession number NRRL 18075, said culture being capable of producing antibiotic LL-D42067α in recoverable quantities upon fermentation in an aqueous nutrient medium containing assimilable sources of carbon, nitrogen and inorganic anion and cation salts.

4. The biologically pure culture of the microorganism *Micromonospora purpureochromogenes* ssp. Wuxiensis according to claim 3, wherein said microorganism has spontaneously mutated, such that the microorganism is genetically altered but still retains the ability to synthesize antibiotic LL-D42067α.

5. The biologically pure culture of the microorganism *Micromonospora purpureochromogenes* ssp. Wuxiensis, according to claim 3, wherein said microorganism has been subjected to mutagenic means such that the microorganism is genetically altered but still retains the ability to synthesize antibiotic LL-D42067α.

* * * * *